United States Patent
Olsen et al.

(10) Patent No.: US 7,766,860 B2
(45) Date of Patent: Aug. 3, 2010

(54) CATHETER SYSTEMS HAVING FLOW RESTRICTORS

(75) Inventors: James M. Olsen, Plymouth, MN (US); Mary M. Morris, Mounds View, MN (US); Michael Hegland, Mounds View, MN (US); Justin A. Blanco, Philadelphia, PA (US)

(73) Assignee: Medtronic, Inc., Minneapolis, MN (US)

( * ) Notice: Subject to any disclaimer, the term of this patent is extended or adjusted under 35 U.S.C. 154(b) by 635 days.

(21) Appl. No.: 11/112,077

(22) Filed: Apr. 22, 2005

(65) Prior Publication Data

US 2005/0245887 A1 Nov. 3, 2005

Related U.S. Application Data

(60) Provisional application No. 60/564,473, filed on Apr. 22, 2004.

(51) Int. Cl.
*A61M 1/00* (2006.01)
(52) U.S. Cl. .......................... 604/34; 604/246
(58) Field of Classification Search .............. 604/284, 604/173, 9, 31, 65, 256, 536, 537, 8, 96.01, 604/101.03, 102.03, 103.8, 103.01, 103.05, 604/30, 34, 274, 246; 222/481; 137/40, 137/493, 559, 843; 138/40, 43; 251/342
See application file for complete search history.

(56) References Cited

U.S. PATENT DOCUMENTS

| | | | |
|---|---|---|---|
| 3,626,959 A * | 12/1971 | Santomieri ................... 137/1 |
| 3,671,979 A | 6/1972 | Moulopoulos |
| 3,951,147 A * | 4/1976 | Tucker et al. .............. 604/891.1 |
| 4,176,683 A * | 12/1979 | Leibinsohn ................. 137/559 |
| 4,397,335 A * | 8/1983 | Doblar et al. ............ 137/625.19 |
| 4,411,292 A | 10/1983 | Schiller |
| 4,550,748 A * | 11/1985 | Nunez ....................... 137/605 |
| 4,759,752 A * | 7/1988 | Stober ....................... 604/247 |
| 4,798,226 A * | 1/1989 | Struth ..................... 137/512.4 |
| 4,834,704 A * | 5/1989 | Reinicke .................... 604/508 |
| 5,006,997 A | 4/1991 | Reich |
| 5,279,544 A | 1/1994 | Gross et al. |
| 5,342,298 A | 8/1994 | Michaels et al. |
| 5,395,352 A * | 3/1995 | Penny ....................... 604/256 |
| 5,531,684 A | 7/1996 | Ensminger et al. |

(Continued)

FOREIGN PATENT DOCUMENTS

EP 0 564 321 A 10/1993

(Continued)

*Primary Examiner*—Nicholas D Lucchesi
*Assistant Examiner*—Laura A Bouchelle
(74) *Attorney, Agent, or Firm*—Mueting, Raasch & Gebhardt, P.A.

(57) ABSTRACT

Catheter systems including one or more flow restrictors are disclosed. The catheter systems may include two or more delivery branches. The delivery branches may be connected to a supply catheter section using a branching catheter connector that may include one or more flow restrictors. The flow restrictors may include a restrictor body located within a lumen with a channel located between the restrictor body and interior surface of the lumen, the channel restricting flow through the lumen past the flow restrictor. The channel may be defined by a groove formed in the restrictor body and/or the interior surface of the lumen. Methods of providing pressure relief by flowing fluid past a flow restrictor are also disclosed.

51 Claims, 7 Drawing Sheets

U.S. PATENT DOCUMENTS

| | | |
|---|---|---|
| 5,558,640 A | 9/1996 | Pfeiler et al. |
| 5,605,545 A | 2/1997 | Nowosielski et al. |
| 5,746,722 A * | 5/1998 | Pohndorf et al. ............ 604/175 |
| 5,820,589 A | 10/1998 | Torgerson et al. |
| 5,893,838 A | 4/1999 | Daoud et al. |
| 5,899,873 A | 5/1999 | Jones et al. |
| 5,928,195 A | 7/1999 | Malamud et al. |
| 5,999,857 A | 12/1999 | Weijand et al. |
| 6,179,806 B1 | 1/2001 | Sansoucy |
| 6,203,523 B1 | 3/2001 | Haller et al. |
| 6,551,290 B1 * | 4/2003 | Elsberry et al. ............ 604/284 |
| 6,585,681 B2 | 7/2003 | Brugger et al. |
| 6,689,085 B1 * | 2/2004 | Rubenstein et al. ............ 604/9 |
| 6,749,581 B2 | 6/2004 | Thompson et al. |
| 6,893,429 B2 | 5/2005 | Petersen |
| 6,945,969 B1 | 9/2005 | Morris et al. |
| 7,217,251 B2 | 5/2007 | Olsen et al. |
| 2002/0107471 A1 | 8/2002 | Thompson et al. |
| 2004/0199128 A1 | 10/2004 | Morris et al. |
| 2005/0075624 A1 | 4/2005 | Miesel |
| 2005/0090799 A1 | 4/2005 | Morris |
| 2005/0241387 A1 | 11/2005 | Miesel et al. |
| 2005/0245858 A1 | 11/2005 | Miesel et al. |
| 2005/0245867 A1 | 11/2005 | Olsen et al. |

FOREIGN PATENT DOCUMENTS

| | | |
|---|---|---|
| EP | 0 873 762 A | 10/1998 |
| EP | 0 968 732 A | 1/2000 |
| WO | WO 9821419 A1 * | 5/1998 |

* cited by examiner

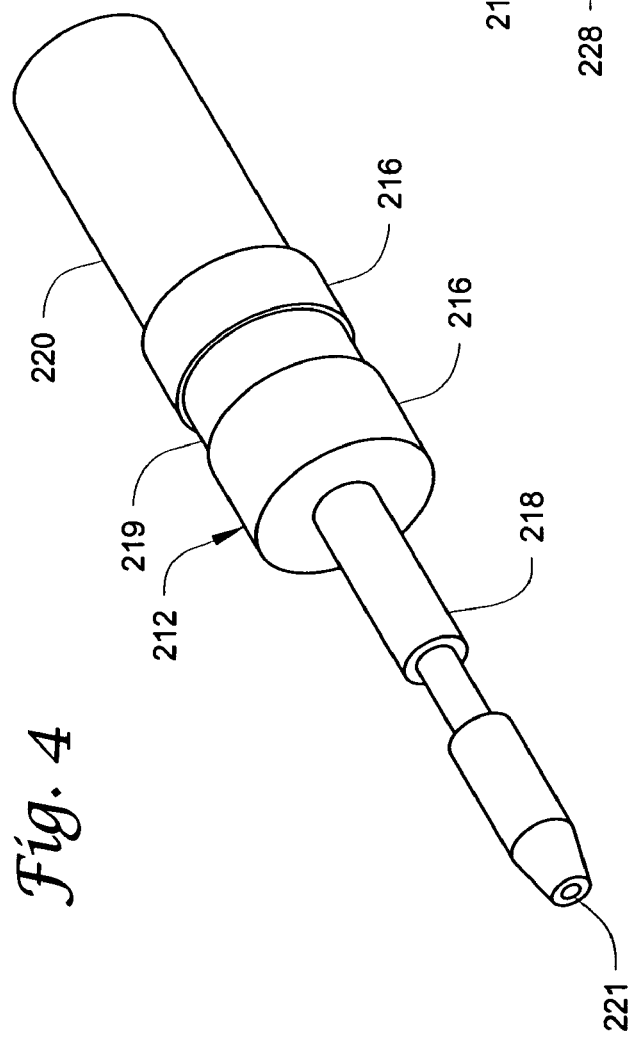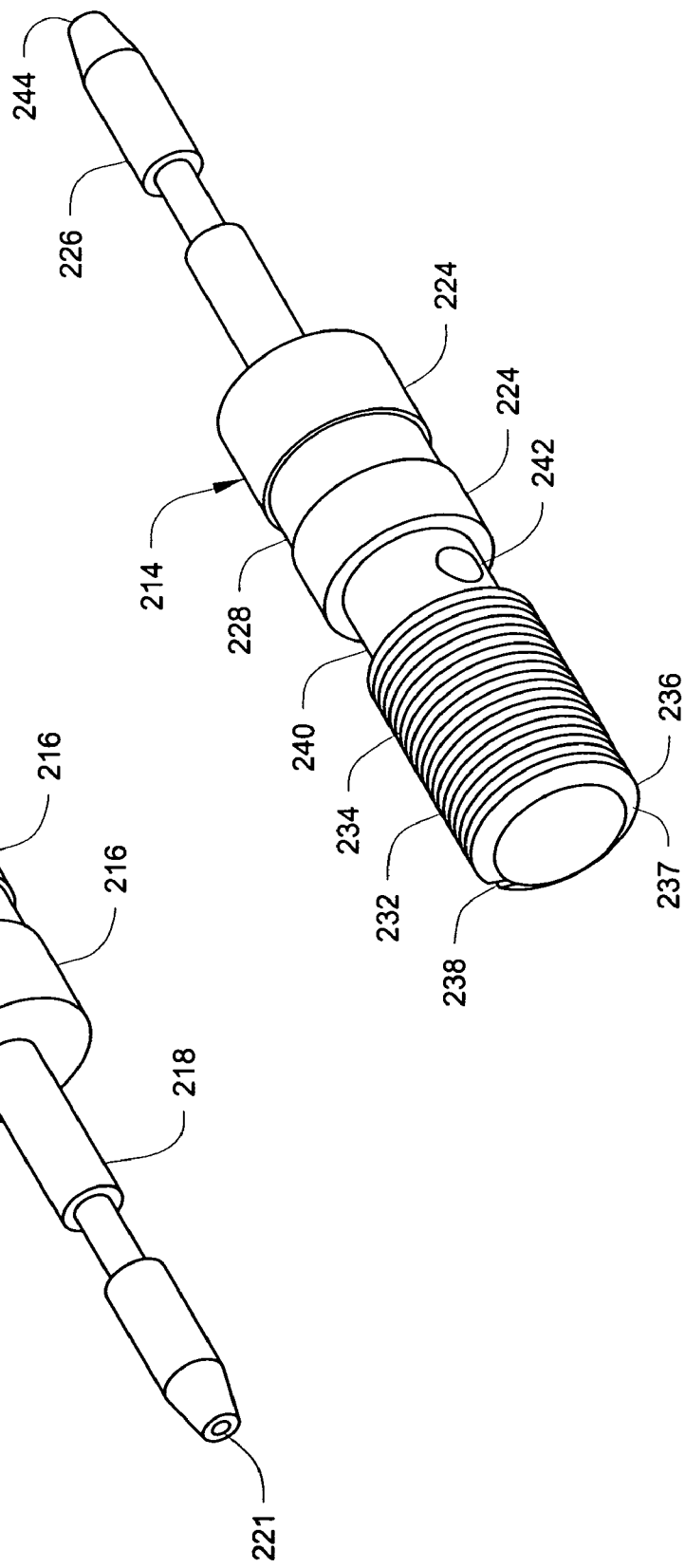

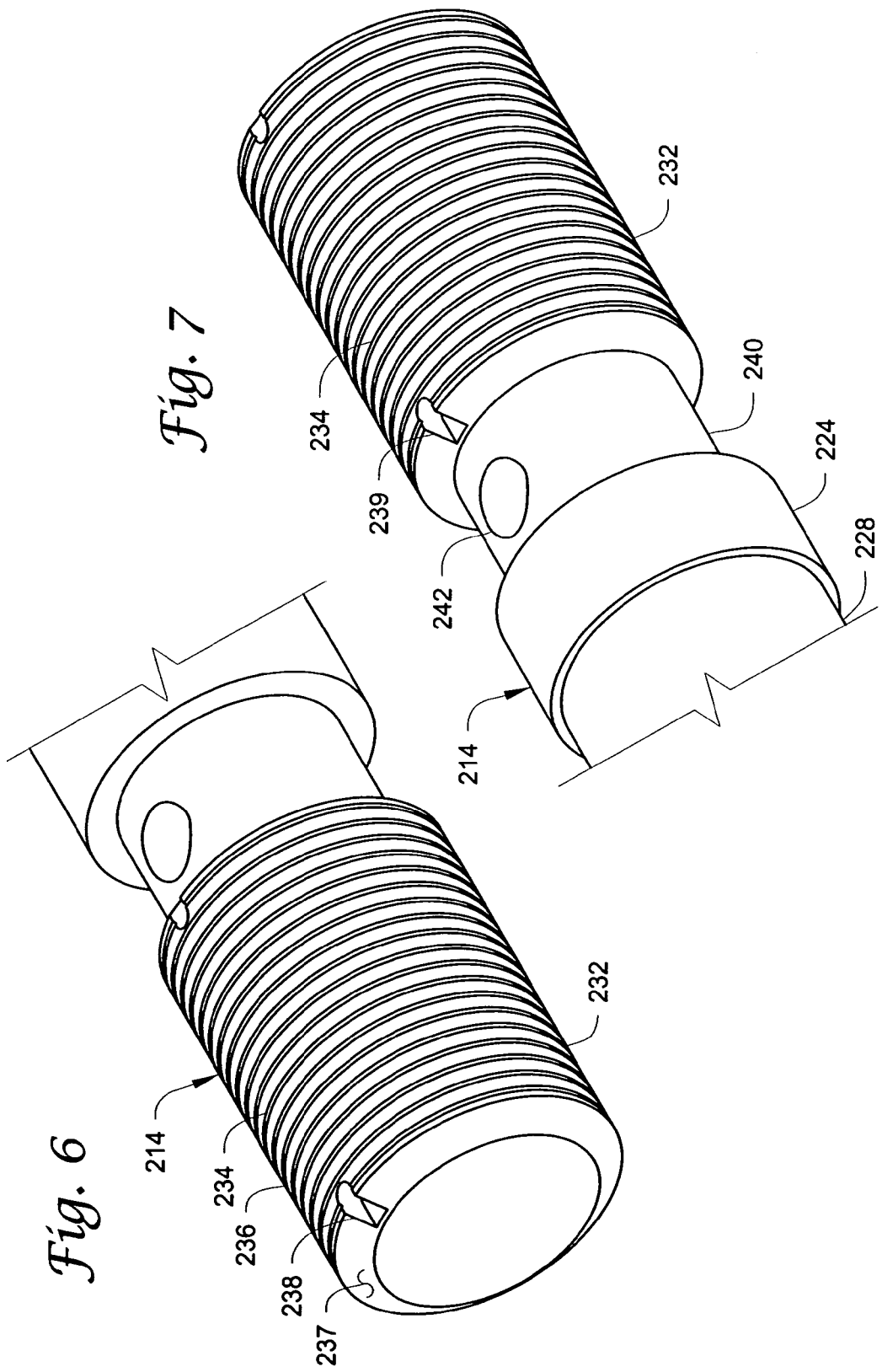

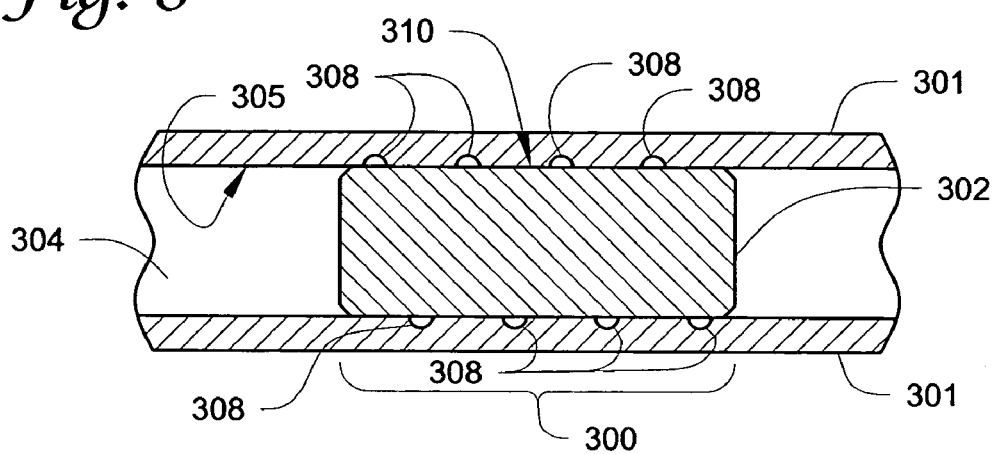
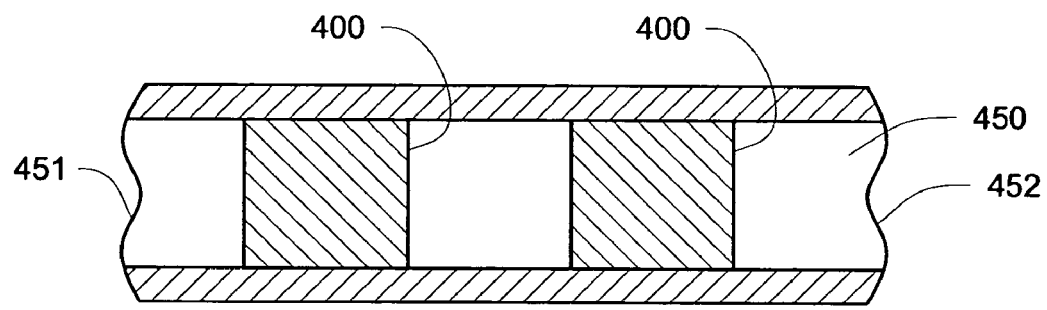
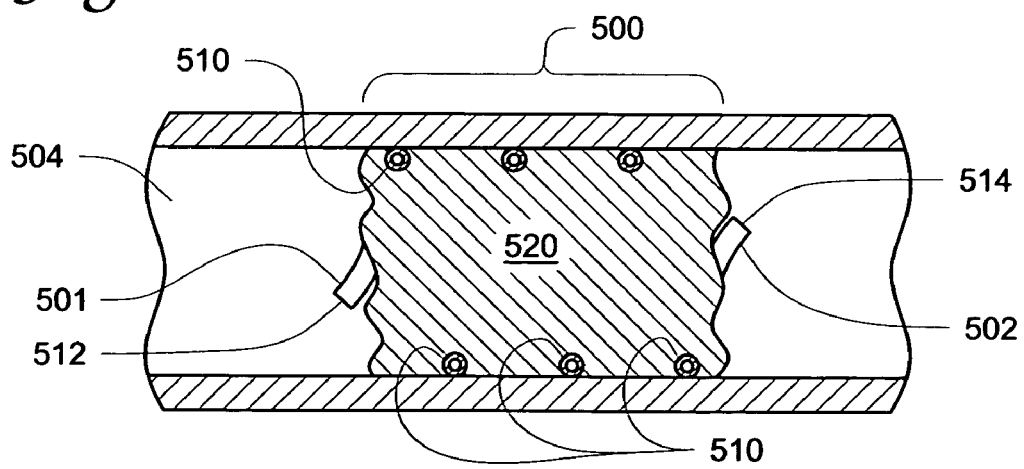

CATHETER SYSTEMS HAVING FLOW RESTRICTORS

RELATED APPLICATION

This application claims the benefit of U.S. Provisional Application No. 60/564,473, titled CATHETER SYSTEM HAVING FLOW RESTRICTION, AND DIAGNOSTIC SYSTEM FOR USE WITH SAME, filed Apr. 22, 2004, which is hereby incorporated by reference in its entirety.

TECHNICAL FIELD

The present invention relates generally to implantable medical devices and, more particularly, to flow restrictors in medical catheters and branching catheter connectors incorporating one or more flow restrictors.

BACKGROUND

Implantable infusion systems are used to provide programmable long-term delivery of a therapeutic agent, e.g., infusate drug, to a target site such as the brain or the spinal canal or epidural space. These systems typically include a pump implanted at a remote location, e.g., within the abdominal or chest cavity, and a catheter tunneled from the pump to the target site. A drug may be delivered from a reservoir in the pump to the target site via the catheter.

Some therapies, e.g., treatment of many neurological diseases, may benefit from infusion of a therapeutic agent to multiple locations within the body. For instance, for the treatment of Parkinson's Disease, it may be beneficial to deliver a substance, e.g., Glial Derived Neurotrophic Factor (GDNF), to both hemispheres of the brain (bilaterally). Infusing a drug to such multiple target sites is typically accomplished by separate infusion systems, e.g., a separate pump and catheter system for each target site. However, duplicate systems result in not only increased costs and patient invasiveness (as compared to single target site systems), but also increased complexity that is inherent in such dual systems.

SUMMARY OF THE INVENTION

The present invention is directed to catheter systems including one or more flow restrictors for use with the same. The catheter systems may include two or more delivery branches. The delivery branches may be connected a supply catheter using a branching connector. Methods of delivering a drug via catheter systems of the invention, e.g., a branching catheter system, to multiple target locations within a body are also provided.

In one embodiment, a flow restrictor for use with an implantable catheter system is provided. The flow restrictor may include a restrictor body having one or more helical grooves formed in an outer surface thereof. The flow restrictor body is located within a lumen of the catheter such that the one or more grooves form channels with the interior surface of the lumen. Fluid flow through the channel or channels is preferably restricted because of the limited cross-sectional size of the channel or channels.

Although it may be preferred that the groove or grooves in the flow restrictor body form the flow-restricted channel or channels in combination with the interior surface of the lumen, in some embodiments, the flow restrictor may be provided using a body located within a separate sheath. The interior surface of the sheath is then used in combination with the groove or grooves in the restrictor body to form the flow restricted channel or channels. The combined flow restrictor body and sheath may then be inserted within the catheter lumen.

In another alternative, one or more grooves may be formed in the interior surface of the lumen in which a flow restrictor body is located while the outer surface of the restrictor body is substantially smooth. In such an embodiment, the groove or grooves in the interior surface of the lumen, together with the smooth outer surface of the restrictor body, define one or more channels extending from an upstream end of the flow restrictor body to the downstream end of the flow restrictor body.

In still another alternative, both the interior surface of the lumen and the outer surface of the flow restrictor body may each include one or more grooves formed therein. In such an embodiment, the grooves in the surfaces facing each other may preferably cooperate to form one or more channels that allow for fluid flow from the upstream end of the restrictor body to the downstream end of the restrictor body.

In another embodiment, a branching catheter connector for use in bifurcating flow in an infusion system is provided. The connector may include in inlet port and at least two outlet ports. Each outlet port may include a flow restrictor associated therewith. In some embodiments, the connector may further include a filter element. The flow restrictors may generate backpressure and maintain substantially equivalent flow through a distal catheter coupled to each outlet port.

In yet another embodiment, a method for delivering a substance to two locations in a body is provided. The method includes delivering the substance to a branching catheter connector through a primary or proximal catheter. The branching catheter connector may, e.g., bifurcate flow of the substance to a first and a second leg. Each of the first and second legs may include a flow restrictor to assist in maintaining substantially equal flow through both the first and second legs. First and second distal catheters may couple, respectively, to the first and second legs. In some embodiments, the substance may be filtered prior, or subsequent, to flow bifurcation.

Although bifurcated catheter connectors are described herein, catheter connectors of the present invention may be used to separate flow into three or more legs of a branching catheter.

Furthermore, although the flow restrictors are described as providing equal flow rates through the different legs of a branched catheter, the flow restrictors of the present invention may provide different flow rates through the different legs by varying the flow restriction provided by the different flow restrictors.

The term "flow restrictor" as used herein, is intended to represent a resistance that is added to a system to bring the total resistance above a specified value; it does not necessarily refer to a singular component. For example, two "flow restrictors" (i.e. two components) of equal resistance placed in series at the tip of a given catheter could be functionally equivalent to a single flow restrictor whose resistance is twice that of either of the series restrictors taken by itself.

The fluids delivered using the present invention preferably contain one or more drugs. A drug of the present invention may include a therapeutic substance. Other substances may or may not be intended to have a therapeutic effect and are not easily classified, such as, e.g., saline solution, fluoroscopy agents, disease diagnostic agents, etc. Unless otherwise noted in the following paragraphs, the term "drug" as used herein may include any therapeutic, diagnostic, or other substance that is delivered using the implantable medical devices of the present invention.

Therapeutic substances delivered using the present invention may preferably be intended to have a therapeutic effect such as pharmaceutical compositions, genetic materials, biologics, and other substances. Pharmaceutical compositions are typically chemical formulations intended to have a therapeutic effect such as intrathecal antispasmodics, pain medications, chemotherapeutic agents, and the like. Pharmaceutical compositions may be configured to function in an implanted environment with characteristics such as stability at body temperature to retain therapeutic qualities, concentration to reduce the frequency of replenishment, and the like. Genetic materials include substances intended to have a direct or indirect genetic therapeutic effect such as genetic vectors, genetic regulator elements, genetic structural elements, DNA, and the like. Biologics include substances that are living matter or derived from living matter intended to have a therapeutic effect such as stem cells, platelets, hormones, biologically produced chemicals, and the like.

In one aspect, the present invention provides a medical catheter that includes a lumen with an interior lumen surface; a flow restrictor located within the lumen, the flow restrictor comprising a restrictor body located within the lumen; and a channel located between an outer surface of the restrictor body and the interior lumen surface of the lumen, wherein the channel extends from an upstream end of the restrictor body to a downstream end of the restrictor body, such that fluid passing through the lumen flows through the channel when the fluid is delivered to the flow restrictor below a selected pressure. In some embodiments, the channel may be defined by a groove formed in the outer surface of the restrictor body, wherein the groove extends from the upstream end to the downstream end of the restrictor body. In other embodiments, the channel may be defined by a groove formed in the interior lumen surface of the lumen, wherein the groove extends from the upstream end to the downstream end of the restrictor body.

In another aspect, the present invention provides a branching catheter connector for use in a branched medical catheter. The connector includes an inlet port and two or more outlet ports in fluid communication with the inlet port. Each of the outlet ports includes an outlet port lumen with an interior surface; a flow restrictor located within the outlet port lumen, the flow restrictor having a restrictor body located within the outlet port lumen; and a channel located between an outer surface of the restrictor body and the interior surface of the outlet port lumen, wherein the channel extends from an upstream end of the restrictor body to a downstream end of the restrictor body, such that fluid passing through the outlet port lumen flows through the channel when the fluid is delivered to the flow restrictor below a selected pressure. In some embodiments, the channel may be defined by a groove formed in the outer surface of the restrictor body, wherein the groove extends from the upstream end to the downstream end of the restrictor body. In other embodiments, the channel may be defined by a groove formed in the interior surface of the outlet port lumen, wherein the groove extends from the upstream end to the downstream end of the restrictor body.

In another aspect, the present invention provides a medical catheter system that includes a lumen and a flow restrictor located within the lumen. The flow restrictor includes one or more capillaries within the lumen, wherein each capillary of the one or more capillaries has a first opening at an upstream end of the flow restrictor and a second opening at a downstream end of the flow restrictor. Each capillary of the one or more capillaries includes one or more coils within the lumen. Fluid passing through the lumen from the upstream end to the downstream end of the flow restrictor flows through the one or more capillaries when the fluid is delivered to the upstream end of the flow restrictor below a selected pressure.

In another aspect, the present invention provides a method of providing pressure relief within a medical catheter system. The method includes providing a medical catheter system that includes a lumen with an interior lumen surface; a flow restrictor located within the lumen, the flow restrictor having a restrictor body located within the lumen; and a channel located between an outer surface of the restrictor body and the interior lumen surface of the lumen, wherein the channel extends from an upstream end of the restrictor body to a downstream end of the restrictor body. The method further includes passing fluid through only the channel from the upstream end of the restrictor body to the downstream end of the restrictor body when fluid pressure within the lumen is below a selected pressure. Pressure relief is provided by passing fluid between the outer surface of the restrictor body and the interior lumen surface of the lumen outside of the channel when fluid pressure is above the selected pressure.

The above summary is not intended to describe each embodiment or every implementation of the present invention. Rather, a more complete understanding of the invention will become apparent and appreciated by reference to the following Detailed Description of Exemplary Embodiments in view of the accompanying figures of the drawing.

BRIEF DESCRIPTIONS OF THE FIGURES

The present invention will be further described with reference to the figures, wherein:

FIG. 4 is a perspective view of an inlet fitting in accordance with one embodiment of the present invention, the inlet fitting operable for use with the branching catheter connector of FIGS. 3A and 3B;

FIG. 5 is a perspective view of an outlet fitting in accordance with one embodiment of the present invention, the outlet fitting operable for use with the branching catheter connector of FIGS. 3A and 3B;

FIGS. 6-7 are enlarged partial perspective views of the outlet fitting of FIG. 5, wherein: FIG. 6 illustrates an upstream end; and FIG. 7 illustrates a downstream portion;

FIG. 8 is a cross-sectional view and alternative embodiment of a flow restrictor according to the present invention;

FIG. 9 is a schematic diagram depicting multiple flow restrictors in a lumen; and FIG. 10 is a cross-sectional view of another alternative flow restrictor according to the present invention.

DETAILED DESCRIPTION OF EXEMPLARY EMBODIMENTS

Figure 1:
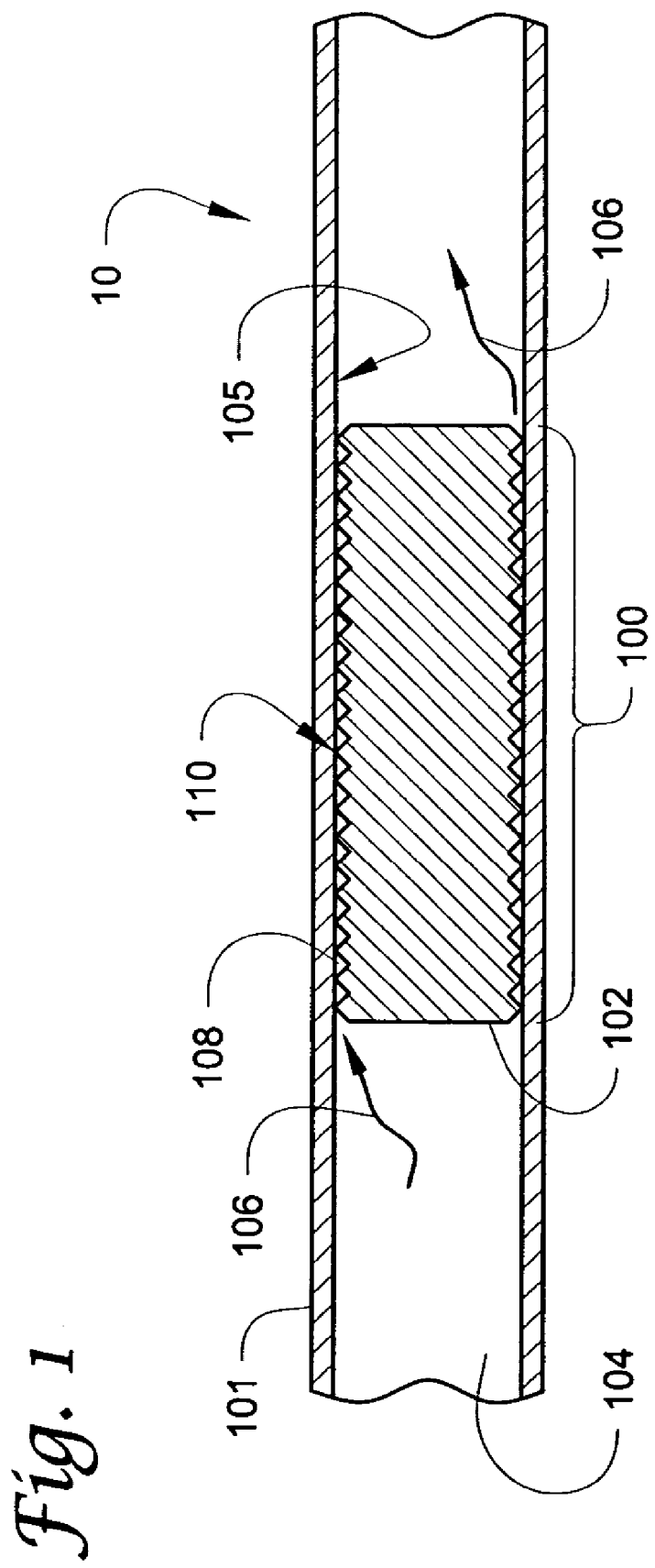
FIG. 1 is a diagrammatic view of a flow restrictor in accordance with one embodiment of the invention, the flow restrictor operable for use in restricting flow of a substance through a tube, e.g., catheter.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Embodiments of the present invention may include flow restrictors for use in fluid delivery tubes, e.g., in implantable medical catheters. These flow restrictors may provide flow resistance to a fluid within the catheter, creating a backpressure therein. By generating such backpressure, various potential benefits may be realized including, for example, the ability to generate diagnostic information as further described below.

Another potential benefit of flow restrictors in accordance with embodiments of the present invention is realized with branching catheter systems that may deliver a substance to two or more separate target areas within a body. Branching catheter systems may divide flow from a first or proximal catheter to two or more legs to which are coupled secondary or distal catheters, e.g., utilizing a "Y" coupling for a bifurcating catheter system. As a result, a single infusion pump may be used to deliver one or more drugs to multiple locations within a body. To provide substantially equal flow to each distal catheter, embodiments of the branching catheter systems may provide a flow resistor limiting flow through each leg. The flow restrictor may preferably contribute to balancing flow through each leg. In addition, the backpressure created by the flow resistor may preferably allow a sensor, e.g., pressure sensor, associated with the infusion pump to detect when catheter flow is abnormal, e.g., when one or more of the proximal or distal catheters is cut or occluded.

FIG. 1 illustrates a tube, e.g., catheter 10, having a lumen 104. A flow restrictor 100 including a flow restrictor body 102, in accordance with one embodiment of the invention, may be positioned in the lumen 104 as shown. While described herein in the context of catheters, those of skill in the art will realize that the flow restrictors described herein may find application in most any tubing application that could benefit from flow resistance.

For simplicity, the catheters (e.g., catheter 10) and flow restrictors (e.g., flow restrictor body 102) are described herein as being generally cylindrical in shape. However, this configuration is not limiting, and embodiments having different shapes are certainly possible without departing from the scope of the invention. For example, the catheters and flow restrictors may include cross-sectional profiles that are triangular, oval, elliptical, hexagonal, semicircular, etc.

The flow restrictor body 102 may substantially block the lumen 104 of the catheter 10 as illustrated. However, a fluid 106 may pass the restrictor 100 by entering a groove 108 formed, in the depicted embodiment, in an outer surface 110 of the flow restrictor body 102. While the depicted groove 108 is helical in form, it should be understood that the groove or grooves used in connection with the present invention may or may not be helical. Grooves with helical or other paths may be useful for increasing the length of the flow path for a given length along a longitudinal axis extending along the direction of fluid flow through the lumen 104.

While only a single groove 108 is illustrated, other embodiments may use multiple grooves where appropriate, e.g., to reduce total flow resistance. If multiple grooves are used, they may intersect with each other at one or more locations or they may not intersect. Moreover, other factors, e.g., groove dimensions and other threadform geometry, surface finish, etc., may be altered to provide the desired flow restriction.

The flow restrictor body 102 may preferably fit tightly, e.g., with an interference fit, within the lumen 104 such that the helical groove 108 effectively forms a channel bounded by the inner diameter of the lumen 104. Accordingly, it may be preferred that the only flow past the flow restrictor body 102 may be through the channel formed by the groove 108 in combination with the interior surface 105 of the lumen 104.

The flow restrictor 100 may provide flow resistance, and thus backpressure, so that a pressure sensor located upstream, e.g., in an infusion pump, can be utilized to detect when the catheter is cut or occluded. That is, by creating a measurable pressure in the lumen 104 upstream of the flow restrictor 100, variations in that backpressure may potentially be utilized to predict occlusions (increased pressure) or leaks (decreased pressure).

Another potential function that may be exhibited by flow restrictors of the present invention is pressure relief. In some embodiments, the flow restrictors of the present invention may preferably allow increased flow in response to pressure increases past a selected relief pressure. For example, the walls 101 of the lumen 104 may be made of materials that exhibit elastic properties that allow for expansion of the lumen 104 (e.g., expansion of the diameter of the lumen for circular lumens) in response to increased pressure upstream of the flow restrictor. Expansion of the lumen 104 may allow fluid to flow between the outer surface 110 of the flow restrictor body 102 and the interior surface 105 of the lumen 104 outside of the groove 108 (or grooves if multiple grooves are present).

In an alternative embodiment that may provide pressure relief function in situations where, e.g., the interior of the lumen is inextensible, the flow restrictor body 102 may be compressible in response to increases in pressure of the fluid flowing past the flow restrictor 102. In such an embodiment, the outer diameter of the outer surface 110 of the flow restrictor body 102 may decrease in response to fluid pressure, thus allowing fluid to flow between the outer surface 110 of the flow restrictor body 102 and the interior surface of the lumen 104 outside of the groove 108 (or grooves if multiple grooves are present).

In still another alternative, pressure relief functions may be provided by embodiments that include both an expandable lumen 104 and a compressible flow restrictor body 102.

The flow restrictors of the present invention may also be incorporated into branching catheter connector, e.g., a flow restrictor 100 may be located so as to limit fluid flow in each outlet leg of a branching catheter system. In this application (discussed in more detail below), the flow restrictors 100 may help to control (e.g., equalize or balance) the flow to each catheter branch in the event of, e.g., partial obstruction at one or both fluid outlets.

Figure 2:
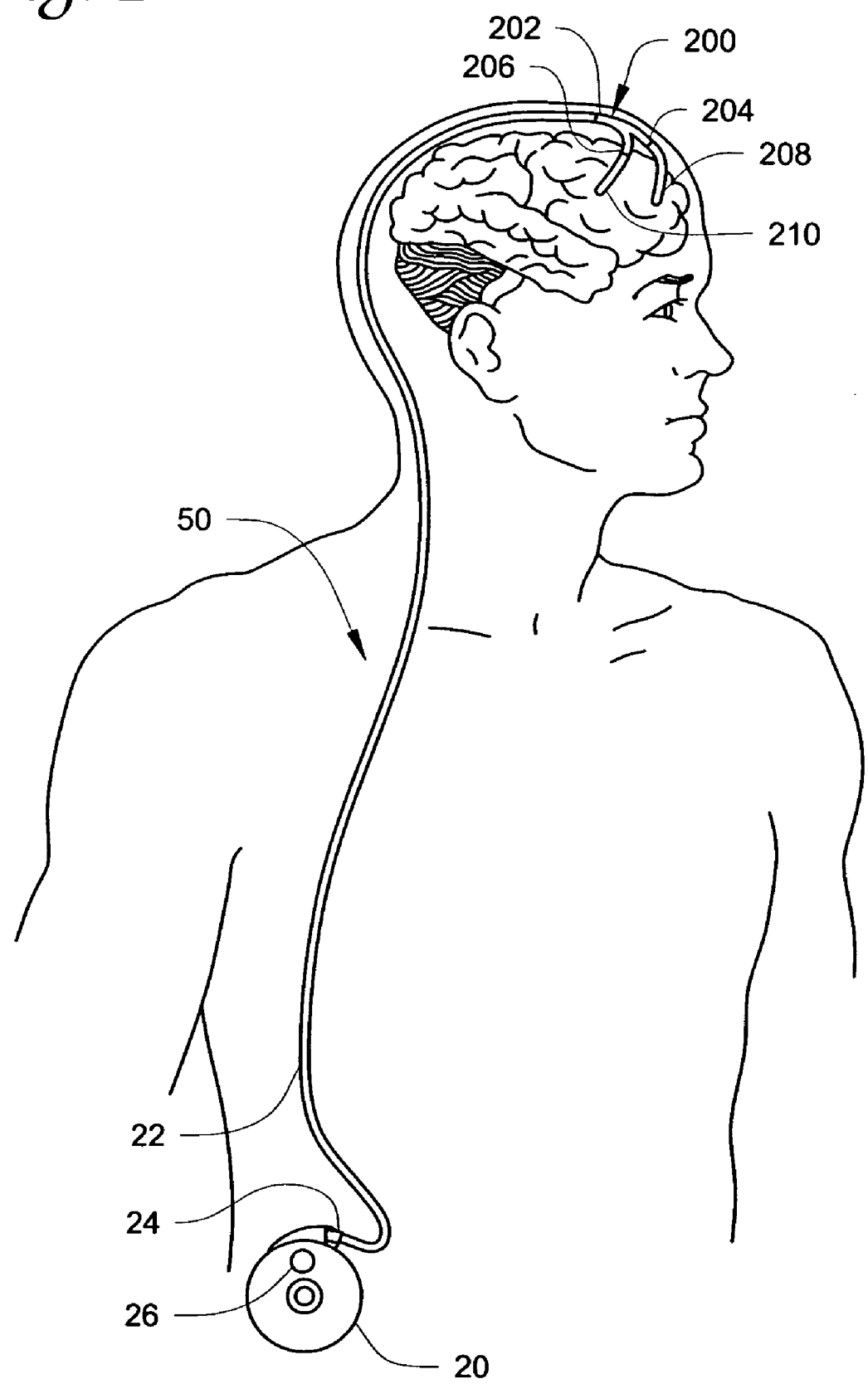
FIG. 2 is a diagrammatic representation of an implanted branching catheter system in accordance with one embodiment of the invention.

FIG. 2 illustrates an exemplary implanted branching catheter system 50 in accordance with one embodiment of the invention. The system 50 may include a device, e.g., a pump 20, implanted in an abdominal region of a patient, and a proximal infusion catheter 22, coupled to the pump 20 via a connector 24. The proximal catheter 22 may extend into the head of the patient, where it may then couple to an inlet port 202 of a branching catheter connector 200. The connector 200 may bifurcate flow to two outlet ports 204 and 206, which are, in turn, coupled to two distal catheters 208 and 210, respectively, implanted in separate areas of the brain.

Although the embodiment of FIG. 2 includes a bifurcating catheter system, the present invention may include catheter systems with three or more branches. In other variations, although the depicted system is implanted for delivery into the brain of a patient, it should be understood that branching catheter systems of the present invention may be used to deliver fluids to other areas of the body.

The pump 20 may include a reservoir to hold a volume of fluid (preferably liquid) containing one or more drugs. The reservoir may be periodically refilled via an injection port (not shown), and a pump mechanism (e.g., pressurized bladder, peristaltic pump, piston pump, etc.) provided may propel the fluid through the proximal and distal catheters 22 and 208, 210. While not wishing to be bound to any particular configuration, the pump 20 may be a SYNCHROMED II manufactured by Medtronic, Inc., of Fridley, Minn., USA.

The pump 20 may further include a flow sensing device, e.g., a pressure sensor 26. The pressure sensor may be similar to that described in U.S. Patent Application Publication No. US 2005/0075624 A1, entitled "Pressure Sensor for Medical Device" (see also: U.S. patent application Ser. No. 10/691,814, filed 23 Oct. 2003, and entitled "Method for Monitoring Bolus Delivery;" U.S. Pat. No. 6,551,290, entitled "Catheter for Target Specific Drug Delivery;" and U.S. patent application Ser. No. 09/625,751, filed 26 Jul. 2000, and entitled "Catheter for Target Specific Drug Delivery").

Figure 3A:
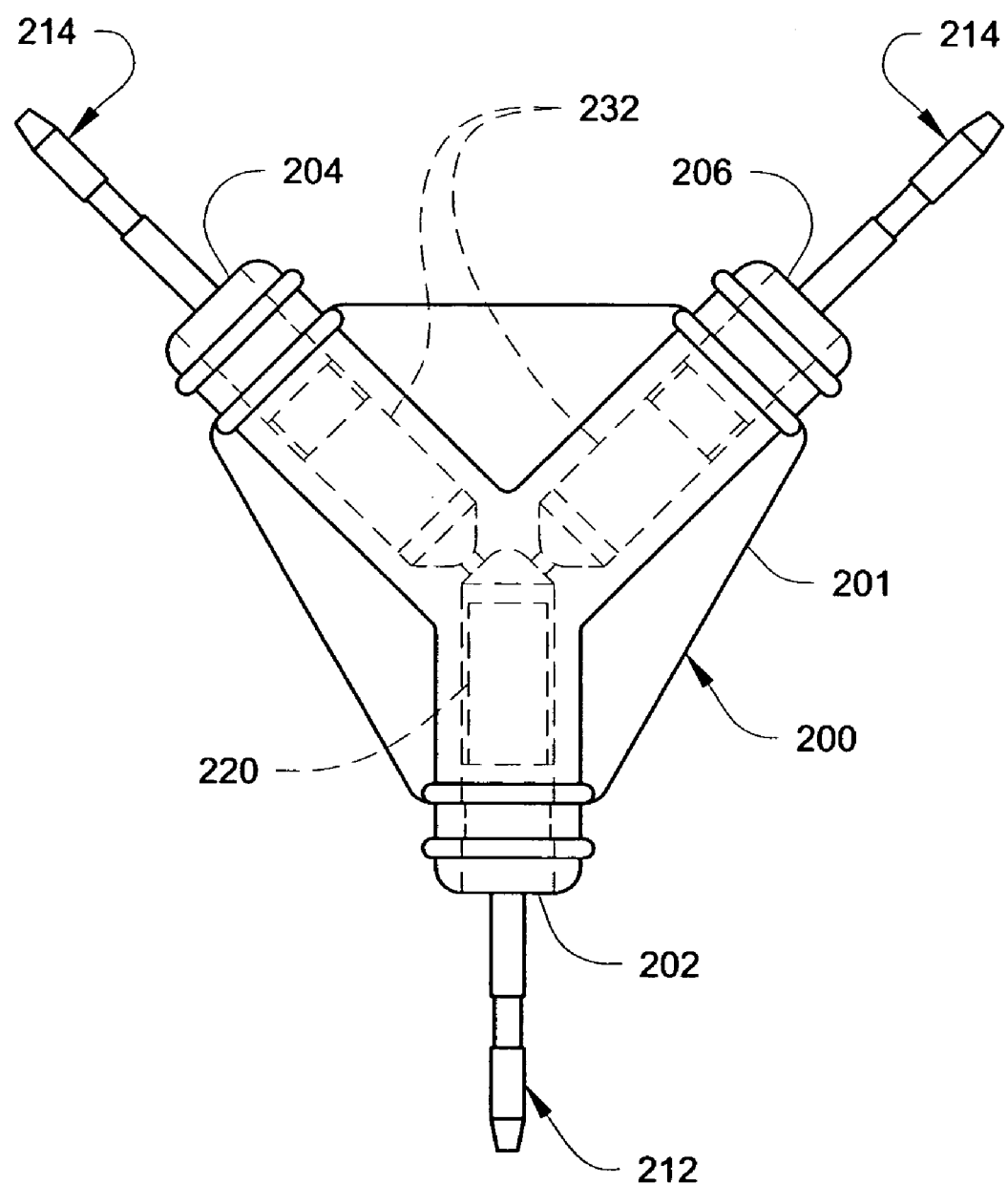
FIG. 3A is a plan view of a branching catheter connector in accordance with one embodiment of the invention.
Figure 3B:
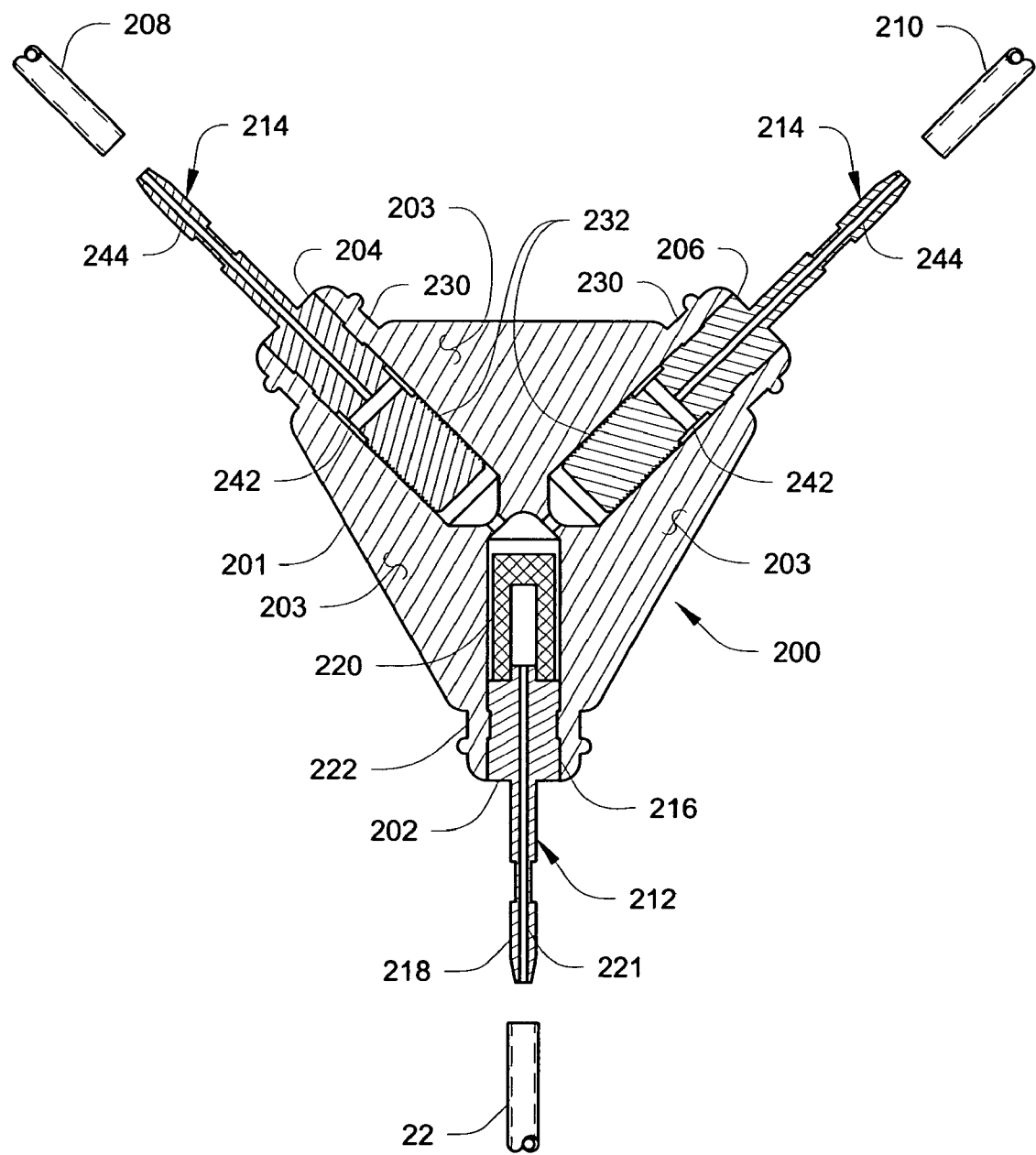
FIG. 3B is a section view of the branching catheter connector of FIG. 3A.

The catheter system may preferably include a branching catheter connector 200 that is used to divide flow to the different branches. FIG. 3A is a top plan view of one embodiment of a branching catheter connector 200 and FIG. 3B is the same in cross-section. Components within the connector may be at least partially visualized in FIG. 3A if the materials of the catheter connector 200 are transparent or translucent.

Referring back to FIG. 2, although the branching catheter connector 200 is depicted as being separated from the pump 20 by the supply catheter 22 which delivers fluid to the inlet port 202, flow restriction could alternatively be provided at the pump 20 such that the pump 20 feeds directly into the inlet port 202 of the connector 200. In such an embodiment, the separate catheters for each branch may extend to the target sites without the need for subsequent branching.

As illustrated in these views, a bifurcating connector 200 such as that depicted may preferably form a generally Y-shaped device having a lumen that starts at the proximal inlet port 202 and then branches to both the first (or left) outlet port 204 and the second (or right) outlet port 206. The outlet ports 204 and 206 may couple, respectively, to the first (or left) distal catheter 208 and the second (or right) distal catheter 210 (see FIGS. 2 and 3B).

The included angle between the outlet ports 204 and 206 is illustrated and described herein as about 90 degrees. However, embodiments wherein the included angle is different, e.g., 0 degrees (outlets are parallel) or 180 degrees (a "T" shaped connector), etc., are certainly possible without departing from the scope of the invention.

The connector body may, in one embodiment, be made from molded silicone (e.g., Nu-Sil MED 4870 LSR, 65-75 Shore A durometer). This material may provide certain potentially desirable benefits, e.g., desirable material properties such as elastic and creep characteristics, at a relatively low cost. However, other biocompatible materials such as ETR silicone, urethane, polyurethane, etc., are also possible without departing from the scope of the invention.

An inlet fitting 212 may be inserted into the inlet port 202 as illustrated herein, while an outlet fitting 214 may be inserted into each outlet port 204 and 206. The inlet fitting 212 is shown in FIG. 4, while the outlet fitting 214 is shown in FIG. 5.

The inlet fitting 212 may preferably include an enlarged portion(s) 216 having an external dimension or diameter that fits within the inlet port 202 with an interference fit. The inlet fitting 212 may also include a pin portion 218 operable to insert into the lumen of a supply or proximal catheter (e.g., catheter 22 as depicted in FIG. 2) with an interference fit.

As used herein, the phrase "interference fit" refers to the coupling of a male member having a dimension larger than an undeflected or undeformed dimension of a mating female receptacle such that one or both of the male and female members deforms during assembly. As a result, a substantially tight and leak-free fit may be obtained once the parts are assembled.

A filter 220 may preferably be attached to, or integrally formed with, the inlet fitting 212. In one embodiment, the inlet fitting 212 may preferably be made from titanium with the filter 220 being a sintered titanium member welded to the fitting 212. However, other embodiments wherein the filter 220 is a separate component, e.g., fits within the fitting, or embodiments wherein one or both of the filter and the fitting 212 are made from other biocompatible materials, e.g., polysulfone, polycarbonate, ethylene tetrafluoroethylene (ETFE), etc., may also be used without departing from the scope of the invention. Regardless of the exact location of the filter 220, it may preferably be located within the flow path between a pump and outlet ports 204 and 206 such that fluids passing into the branches through outlet ports 204 and 206 must pass through the filter before entering the branches.

As shown in FIG. 3B, the filter 220 may preferably be a cup-shaped member having its inner surface in fluid communication with a lumen 221 of the inlet fitting 212 which, in turn, is in fluid communication with a supply or proximal catheter (e.g., catheter 22 as depicted in FIG. 2). The cup-shape of the filter 220 may provide increased surface area (and, thus, potentially increased filtering capacity) over which to filter the passing fluid. To further improve fluid passage through the filter 220, it may be preferable that a gap exist between the outer surface of the filter and the inner surface of the inlet port 202 of the connector 200. However, such a configuration is not required. In fact, filters of most any configuration are possible without departing from the scope of the invention. For instance, a flat porous disc or plug could be used in place of the cup-shaped filter depicted in FIG. 3B.

The micron rating of the filter 220 may preferably be selected to reduce the likelihood that downstream flow restrictors used to control fluid flow through the branches will not occlude with debris. In one exemplary embodiment, the filter 220 may have a micron rating of about 5 microns.

It may be preferred that the filter or filters be positioned upstream of any point at which fluid flow is divided for delivery into the different branches of the branched catheter system. In the depicted embodiment, the location of the inlet filter 220 may be beneficial to ensure that occlusion of the filter pores has an essentially equivalent effect on flow to both branches (i.e., both outlet ports 204 and 206) of the connector 200. However, other configurations that replace the filter 220 with branch filters or, alternatively, utilize staged filters are contemplated.

To assist with retaining the inlet fitting 212 within the connector 200, the inlet fitting may preferably be provided with a depressed portion 219 that may preferably align with a suture groove 222 formed in the connector 200 when assembled. Thus, when a suture is used to secure the connector 200 to tissue, additional resistance to separation of the fitting 212 from the connector 200 may be obtained.

FIG. 5 illustrates the exemplary outlet fitting 214 that may be located in each of the outlet ports 204 and 206. Like the inlet fitting 212, each outlet fitting 214 may include enlarged portions 224 that engage their respective outlet port 204 or 206 with an interference fit. A pin portion 226 may also be provided to insert into the respective distal catheter (208 or 210) with an interference fit. A depressed portion 228, located to correspond to a suture groove 230 when assembled, may be provided in the outlet fitting 214 to allow suture attachment at the groove 230 to contribute to pull-out resistance of the outlet fitting 214 from the connector 200.

A flow restrictor may also be provided within each outlet port 204 and 206 of the connector 200. Like the flow restrictor body 102 described above, each flow restrictor may preferably include a flow restrictor body 232 having a groove 234 (preferably helical) formed in an outer surface 236. The helical groove 234 may provide a fluid pathway having a predetermined flow resistance by virtue of its small effective diameter, e.g., its groove geometry.

The outer surface 236 of the flow restrictor body 232 may preferably fit inside the outlet port 204 and 206 with an interference fit sufficient to ensure reliable sealing under all anticipated flow rates and pressures. Alternatively, other embodiments could configure the interface between the output port 204 (or 206) and the outer surface 236 to mimic a pressure-relief valve, e.g., the portion of the body 201 defining the lumen of each outlet port 204 and 206 could swell sufficiently that, at a particular threshold pressure, a bypass of the restriction is created. Stated another way, at a certain threshold backpressure, the lumen of each outlet port in the body 201 could expand sufficiently to permit fluid to pass between the outer surfaces 236 of the flow restrictor bodies 232 and the interior surfaces of the lumens of outlet ports 204 and 206 outside of the channels created by grooves 234 of restrictors 232 (sometimes referred to as blow-by), thereby reducing backpressure to within acceptable ranges.

FIGS. 6 and 7 are enlarged views of an upstream end and a downstream end, respectively, of the flow restrictor body 232 of one of the outlet fittings 214. In the embodiments illustrated herein, see e.g., FIG. 6, the upstream end may include features, e.g., a notch 238 and a chamfer 237 that may assist fluid in entering the groove 234. The notch 238 and/or chamfer 237 may be produced by, for example electrical discharge machining (EDM), conventional machining, or chemical etching. In some embodiments, the notch 238 and/or chamfer 237 may be optional, e.g., the thread may be sufficiently deep that these features provide no additional benefit. In other embodiments, more than one notch 238 may be provided at the upstream end of the flow restrictor body 232.

Similarly, as shown in FIG. 7, the downstream end of the flow restrictor body 232 may include features, e.g., one or more notches 239, operable to more easily allow fluid to exit the helical groove 234. The notch 239 (or notches) are optional and may not be provided in some embodiments. Notch 239 may be formed using techniques similar to those used to form notch 238 at the upstream end of the flow restrictor body 232.

After exiting the flow restrictor, fluid may preferably enter a reduced section 240 of the outlet fitting 214. The reduced section 240 may provide increased clearance between the fitting 214 and the interior surface of the lumen in each outlet port 204 or 206. Once fluid has entered the reduced section 240, it may preferably flow through a transverse passageway 242, which is preferably in fluid communication with a fitting lumen 244 (see, e.g., FIG. 5) of the outlet fitting 214. The passageway 242 may preferably be oriented perpendicular to a centerline of the outlet fitting 214 (where the centerline is defined by the direction of fluid flow through the fitting lumen 244). It may be preferred that the fitting lumen 244 include a proximal end into which the passageway 242 feeds and a distal end from which fluid flows out of the outlet fitting 214 (in the direction of the arrow seen in FIG. 5).

As illustrated in FIG. 3B, the passageway 242 may pass completely through the fitting 214, e.g., there may be multiple entries into passageway 242 (e.g., on opposing sides) of the fitting 214. In an alternative embodiment, the passageway 242 may be blind, e.g., it may intersect the lumen 244 but not penetrate the opposite side of the fitting 214. In other alternatives, more than two openings may be provided to allow fluid to pass into the fitting lumen 244 from the flow restrictor.

The flow restrictor body 232 and body of the outlet fitting 214 may, in one embodiment, be a unitary part such that the bodies are provided as a one-piece, completely integral unit (e.g., machined as a single component from a single block of material). Such a construction may provide ease of assembly (e.g., low risk of damaging or clogging threads via handling) and improved resistance to pullout upon attachment and/or removal of distal catheters 208 and 210. However, designs in which the restrictor and fitting are separate components are within the scope of the present invention.

The flow restrictors used in the outlet ports 204 and 206 may preferably be configured to provide sufficient backpressure so that any naturally occurring resistance differentials at the target delivery site, e.g., differential resistance caused by partial occlusion in one branch fed by one of the outlet ports, is negligible in comparison. The backpressure created by the flow restrictors may also be relatively large, in comparison to other potential catheter pressure changes, such as those caused by variations in atmospheric or physiologic pressure. As a result, a pressure sensor attached to the catheter system may have an adequate signal-to-noise ratio to accurately distinguish differentials due to cuts/occlusions in the catheters from those changes attributable to these "background" factors.

Referring again to FIGS. 3B and 4-5, one example of flow of infusate through the system will now be described. The infusate may flow from the catheter 22 into the lumen of the inlet fitting 212 where it may then enter the inside of the filter 220. After filtering, the infusate may travel through each branch of the connector 200 until it reaches the flow restrictors 232. The infusate may enter the helical groove 234 via the notch 238 (see FIG. 6) and travel along the channel formed by the groove 234, which is substantially bounded on one side by the interior surface of the outlet ports 204, 206 (the inner lumen of the body 201). The infusate may exit the groove 234 via the notch 239 (see FIG. 7), where it then enters the reduced section 240. The reduced section 240 may preferably be, as described above, stepped-down such that there is clearance with respect to the inner surface of the outlet port 204 (or 206). The infusate fluid may then pass through the passageway 242 and into the lumen 244 of the outlet fitting 214, which is coupled to the distal catheter 208 (or 210).

The body 201 of the connector 200 may preferably include features to ensure that a physician does not place a suture around the flow restrictor body 232 and thereby choke-off flow through the helical groove 234. For example, the body 201 may include gussets or webs 203 (see FIG. 3B) that extend between the outlet ports 204 and 206 that prevent suturing in the location of the flow restrictors 232. Moreover, while the body 201 may provide suture grooves 222 and 230 to assist with preventing inadvertent removal of the inlet fitting 212 and the outlet fittings 214, other retaining features may be substituted or combined without departing from the scope of the invention. For example, raised feature(s) on the inner surface of the inlet and outlet ports could engage corresponding depression(s) on the outer surface of the inlet and outlet fittings. Still further, adhesives could be used to secure the fittings within the ports of the body 201.

In one embodiment, the branching catheter connector 200 may be assembled by first swelling the connector body 201 in a suitable solvent, e.g., hexane or heptane. Once the connector body 201 is adequately swollen, the inlet fitting 212 and outlet fittings 214 may be inserted into the respective inlet ports 202 and outlet ports 204, 206. The inner lumens of the body 201 that define the ports 202, 204, and 206 may be designed with necked-down portions near the center of the body. The necked-down portions may preferably create a palpable stop against which the fittings 212 and 214 may press, thereby reducing the opportunity for over/under insertion of the fittings. Alternatively, other techniques for ensuring proper assembly are contemplated, including, for example, crimp-sleeves and flanges. Once the fittings 212 and 214 are correctly installed, the solvent may be allowed to evaporate. Other methods of assembly such as, for example, press-fitting or heat-shrinking are also contemplated.

Although the flow restrictors described in connection with FIGS. 1 and 3A-7 provide a small channel formed by a groove in the outer surface of a restrictor body, alternative constructions that achieve the same result may be used. One such alternative is depicted in the cross-sectional view of FIG. 8. As seen there, flow restrictor body 302 is located within a lumen 304. The lumen 304 may be in tubing, e.g., a catheter, or it may be formed as a port in a branching catheter connector.

The outer surface 310 of the flow restrictor body 302 in the embodiment of FIG. 8 may preferably be relatively smooth while the interior surface 305 of the lumen 304 may include one or more grooves 308 formed therein. The groove or grooves 308 may preferably, but not necessarily, be helical in shape. As a result, the groove 308 and smooth outer surface 310 of the flow restrictor body 302 may preferably form a small channel that extends from an upstream end of the body 302 to the downstream end of the body 302. That channel allows fluid to pass through the lumen 304 while providing the desired flow restriction.

The variations described herein, such as, e.g., multiple grooves to form multiple channels, other cross-sectional shapes, extensible lumens and/or compressible flow restrictor bodies to provide pressure relief, etc. may also be providing in connection with flow restrictors in which the grooves are formed in the interior lumen surface.

Yet another variation in the flow restrictors of the present invention is that the flow restrictor 100 of FIG. 1 and flow restrictor 300 of FIG. 8 my be provided as unitary articles that may be located within a separate lumen or passageway to provide the desired flow restriction. In other words, the walls 101 forming the lumen 104 and walls 301 forming the lumen 304 may be located within a separate lumen or passageway to provide flow restriction as desired. In such embodiments, the flow restrictors may be provided as, e.g., flow restriction plugs that may be used alone or in groups of two or more to provide a selected level of flow restriction. One such embodiment may be schematically depicted in FIG. 9 in which multiple flow restrictors 400 are provided within a lumen 450.

The flow restrictors 400 may preferably be secured within the lumen 450 (e.g., by an interference fit, welding, etc.) such that fluid moving from the upstream end 451 to the downstream end 452 must move through the flow restrictors 400. The lumen 450 and/or flow restrictors 400 may also possess some extensibility and/or compressibility to provide pressure relief functions as described elsewhere herein.

In yet another embodiment of flow restrictors according to the present invention, flow resistance may be achieved through a coiled capillary that provides a small channel similar to that formed by the grooves of the other flow restrictor embodiments described herein. Capillaries made of, e.g., glass, are available with diameters on the order of, e.g., 0.001 inches (about 0.025 mm). These capillary structures may be coiled with a bend radius and length sufficient to generate the desired flow resistance while maintaining an envelope suitable for implantation. It may be preferred that such capillaries be formed with a substantially uniform bore diameter along their length.

One embodiment of a flow restrictor 500 is depicted in FIG. 10 in which a coiled capillary 510 is located within a lumen 504. The coiled capillary 510 may preferably be held within a plug 520 of material that occludes the remainder of the lumen 504. As a result, fluid moving through the lumen 504 from the upstream end 501 to the downstream end 502 must pass through the coiled capillary 510. The coiled capillary 510 preferably includes an opening 512 proximate the upstream end 501 through which fluid flows into the capillary 510 and a opening 514 proximate the downstream end 502 through which fluid exits from the capillary 510. The capillary 510 may preferably include two or more coils located within the lumen 504 (where each coil passes around 360 degrees within the lumen 504).

Although flow restrictor 500 includes only one capillary 510, flow restrictors 500 may include two or more independent capillaries, each with openings proximate the upstream and downstream ends of the flow restrictor 500 such that fluid can flow therethrough.

From the foregoing, numerous alternative concepts may exist for a flow restrictor(s) that can be placed in the lumen of a drug-infusing catheter. Two or more restrictors may be placed in each leg of a branching catheter system to ensure balanced flow in the event of a catheter malfunction, e.g., partial occlusion or cut at one or both catheter outlets, or an occlusion at most any location along a distal catheter leg.

Example

The following example is provided to illustrate exemplary embodiments of the invention.

A Medtronic SYNCHROMED II pump was used to infuse a saline solution at a rate of about 300 microliters/day ($\mu$L/day)—about 150 $\mu$L/day per side (left and right)—via a catheter branching connector substantially similar to that illustrated in FIGS. 3A and 3B.

The connector incorporated a filter (see, e.g., filter 220) having a 5 micron rating. An outlet fitting (see, e.g., fitting 214 in FIG. 5) incorporating a flow restrictor (see e.g., flow restrictor 232) was also provided. The restrictor included a helical groove (see, e.g., groove 234) formed on a uniform cylindrical portion of the outlet fitting. The flow restrictor had a nominal diameter of about 0.072 inches (about 1.8 mm) and a length of about 0.14 inches (about 3.6 mm). The groove had a nominal depth of about 0.0012 inches (about 0.03 mm), and a pitch of about 250 threads/inch (about 10 threads per mm).

The pump, connector, and related components were then immersed in a 37° C. water bath. Each outlet port of the connector was coupled to a distal catheter that terminated in an oil-capped vessel of water set upon a balance. Catheter backpressure, atmospheric pressure, and the mass of each balance over time were monitored.

Two 72-hour tests were conducted: one in which outlet pressures were equal; and a second having a differential pressure of 0.15 psi (about 1 kPa) across outlets, e.g., across distal catheter tips (brought about by a 4.25 inch (about 11 cm) water head-height difference). The latter was estimated to be a potential implant pressure differential.

Both tests yielded results indicating that flow from each leg of the branching connector was consistently within about 2% of its nominal flow rate of 150 $\mu$L/day. During these tests, the 5 $\mu$m sintered titanium filter remained substantially free from occlusion from the saline solution. Average catheter backpressure during both tests was about 3 psig (about 20 kPa).

As used herein and in the appended claims, the singular forms "a," "and," and "the" include plural referents unless the context clearly dictates otherwise.

Thus, for example, reference to "a" or "the" component may include one or more of the components and equivalents thereof known to those skilled in the art.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein.

The invention claimed is:

1. A medical catheter comprising:
a lumen comprising an interior lumen surface;
a flow restrictor located within the lumen, the flow restrictor comprising a restrictor body located within the lumen; and
a channel located between an outer surface of the restrictor body and the interior lumen surface of the lumen, wherein the channel extends from an upstream end of the restrictor body to a downstream end of the restrictor body, such that fluid passing through the lumen flows through the channel when the fluid is delivered to the flow restrictor below a selected pressure, wherein the channel is defined by a groove formed in the interior lumen surface of the lumen, wherein the groove extends from the upstream end to the downstream end of the restrictor body.

2. A medical catheter according to claim 1, wherein the restrictor body has an interference fit within the lumen.

3. A medical catheter according to claim 1, further comprising a pump mechanism and reservoir in fluid communication with the lumen.

4. A medical catheter comprising:
a lumen comprising an interior lumen surface;
a flow restrictor located within the lumen, the flow restrictor comprising a restrictor body located within the lumen; and
a channel located between an outer surface of the restrictor body and the interior lumen surface of the lumen, wherein the channel extends from an upstream end of the restrictor body to a downstream end of the restrictor body, such that fluid passing through the lumen flows through the channel when the fluid is delivered to the flow restrictor below a selected pressure, wherein the flow restrictor comprises a first notch in the first end of the outer surface of the restrictor body, the first notch in fluid communication with the channel at the upstream end of the restrictor body.

5. A medical catheter according to claim 4, wherein the flow restrictor comprises a second notch in the second end of the outer surface of the restrictor body, the second notch in fluid communication with the channel at the downstream end of the restrictor body.

6. A medical catheter according to claim 4, wherein the restrictor body has an interference fit within the lumen.

7. A medical catheter according to claim 4, further comprising a pump mechanism and reservoir in fluid communication with the lumen.

8. A medical catheter comprising:
a lumen comprising an interior lumen surface;
a flow restrictor located within the lumen, the flow restrictor comprising a restrictor body located within the lumen;
a channel located between an outer surface of the restrictor body and the interior lumen surface of the lumen, wherein the channel extends from an upstream end of the restrictor body to a downstream end of the restrictor body, such that fluid passing through the lumen flows through the channel when the fluid is delivered to the flow restrictor below a selected pressure; and
a fitting body attached to the restrictor body proximate the second end of the restrictor body, wherein the fitting body comprises:
a fitting lumen, at least a portion of which is located within the lumen, the fitting lumen comprising a proximal end proximate the restrictor body and a distal end distal from the restrictor body; and
a transverse passageway in fluid communication with the proximal end of the axial passageway, wherein the transverse passageway comprises an opening proximate the second end of the restrictor body such that fluid exiting the groove at the second end of the restrictor body enters the transverse passageway through the opening and is passed through the axial lumen to the distal end of the fitting body.

9. A medical catheter according to claim 8, wherein the fitting body and the restrictor body are a one-piece, completely integral unit.

10. A medical catheter according to claim 8, wherein the fitting body comprises a suture groove formed in an exterior surface of the fitting body.

11. A medical catheter according to claim 8, wherein the restrictor body has an interference fit within the lumen.

12. A medical catheter according to claim 8, further comprising a pump mechanism and reservoir in fluid communication with the lumen.

13. A medical catheter comprising:
a lumen comprising an interior lumen surface;
a flow restrictor located within the lumen, the flow restrictor comprising a restrictor body located within the lumen; and
a channel located between an outer surface of the restrictor body and the interior lumen surface of the lumen, wherein the channel extends from an upstream end of the restrictor body to a downstream end of the restrictor body, such that fluid passing through the lumen flows through the channel when the fluid is delivered to the flow restrictor below a selected pressure;
wherein the flow restrictor comprises a pressure relief valve such that when the fluid is delivered to the flow restrictor above the selected pressure, fluid flows between the outer surface of the flow restrictor and the interior lumen surface of the lumen outside of the channel.

14. A medical catheter according to claim 13, wherein the restrictor body has an interference fit within the lumen.

15. A medical catheter according to claim 13, further comprising a pump mechanism and reservoir in fluid communication with the lumen.

16. A medical catheter according to claim 13, wherein, when fluid is delivered to the flow restrictor above the selected pressure, fluid flow past the flow restrictor increases as compared to fluid flow past the flow restrictor when the fluid is delivered to the flow restrictor below the selected pressure.

17. A branching catheter connector for use in a branched medical catheter, the connector comprising:
an inlet port; and
two or more outlet ports in fluid communication with the inlet port;
wherein each of the outlet ports comprises:
an outlet port lumen comprising an interior surface;
a flow restrictor located within the outlet port lumen, the flow restrictor comprising a restrictor body located within the outlet port lumen;
a channel located between an outer surface of the restrictor body and the interior surface of the outlet port lumen, wherein the channel extends from an upstream end of the restrictor body to a downstream end of the restrictor body, such that fluid passing through the outlet port lumen flows through the channel when the fluid is delivered to the flow restrictor below a selected pressure, wherein the channel is defined by a groove formed in the outer surface of the restrictor body, wherein the groove extends from the upstream end to the downstream end of the restrictor body.

18. A branching catheter connector according to claim 17 that further comprises a connector body, wherein the inlet port and the two or more outlet ports are located within the connector body, and wherein the connector body comprises one or more suture grooves formed in an exterior surface of the connector body.

19. A branching catheter connector according to claim 17, wherein the inlet port comprises a filter element located therein, wherein fluid passing from the inlet port to any of the two or more outlet ports passes through the filter element.

20. A branching catheter connector according to claim 17, wherein the restrictor body has an interference fit within the outlet port lumen.

21. A branching catheter connector according to claim 17, further comprising a pump mechanism and reservoir in fluid communication with the inlet port.

22. A branching catheter connector for use in a branched medical catheter, the connector comprising:
an inlet port; and
two or more outlet ports in fluid communication with the inlet port;
wherein each of the outlet ports comprises:
an outlet port lumen comprising an interior surface;
a flow restrictor located within the outlet port lumen, the flow restrictor comprising a restrictor body located within the outlet port lumen;
a channel located between an outer surface of the restrictor body and the interior surface of the outlet port lumen, wherein the channel extends from an upstream end of the restrictor body to a downstream end of the restrictor body, such that fluid passing through the outlet port lumen flows through the channel when the fluid is delivered to the flow restrictor below a selected pressure, wherein the channel is defined by a groove formed in the interior surface of the outlet port lumen, wherein the groove extends from the upstream end to the downstream end of the restrictor body.

23. A branching catheter connector according to claim 22, wherein the restrictor body has an interference fit within the outlet port lumen.

24. A branching catheter connector according to claim 22, further comprising a pump mechanism and reservoir in fluid communication with the inlet port.

25. A branching catheter connector for use in a branched medical catheter, the connector comprising:
an inlet port; and
two or more outlet ports in fluid communication with the inlet port;
wherein each of the outlet ports comprises:
an outlet port lumen comprising an interior surface;
a flow restrictor located within the outlet port lumen, the flow restrictor comprising a restrictor body located within the outlet port lumen;
a channel located between an outer surface of the restrictor body and the interior surface of the outlet port lumen, wherein the channel extends from an upstream end of the restrictor body to a downstream end of the restrictor body, such that fluid passing through the outlet port lumen flows through the channel when the fluid is delivered to the flow restrictor below a selected pressure, wherein the channel comprises a helical channel.

26. A branching catheter connector according to claim 25, wherein the restrictor body has an interference fit within the outlet port lumen.

27. A branching catheter connector according to claim 25, further comprising a pump mechanism and reservoir in fluid communication with the inlet port.

28. A branching catheter connector for use in a branched medical catheter, the connector comprising:
an inlet port; and
two or more outlet ports in fluid communication with the inlet port;
wherein each of the outlet ports comprises:
an outlet port lumen comprising an interior surface;
a flow restrictor located within the outlet port lumen, the flow restrictor comprising a restrictor body located within the outlet port lumen;
a channel located between an outer surface of the restrictor body and the interior surface of the outlet port lumen, wherein the channel extends from an upstream end of the restrictor body to a downstream end of the restrictor body, such that fluid passing through the outlet port lumen flows through the channel when the fluid is delivered to the flow restrictor below a selected pressure, wherein the flow restrictor comprises a first notch in the upstream end of the outer surface of the restrictor body, the first notch in fluid communication with the groove at the upstream end of the restrictor body.

29. A branching catheter connector according to claim 28, wherein the flow restrictor comprises a second notch in the downstream end of the outer surface of the restrictor body, the second notch in fluid communication with the groove at the downstream end of the restrictor body.

30. A branching catheter connector according to claim 28, wherein the restrictor body has an interference fit within the outlet port lumen.

31. A branching catheter connector according to claim 28, further comprising a pump mechanism and reservoir in fluid communication with the inlet port.

32. A branching catheter connector for use in a branched medical catheter, the connector comprising:
an inlet port; and
two or more outlet ports in fluid communication with the inlet port;
wherein each of the outlet ports comprises:
an outlet port lumen comprising an interior surface;
a flow restrictor located within the outlet port lumen, the flow restrictor comprising a restrictor body located within the outlet port lumen;

a channel located between an outer surface of the restrictor body and the interior surface of the outlet port lumen, wherein the channel extends from an upstream end of the restrictor body to a downstream end of the restrictor body, such that fluid passing through the outlet port lumen flows through the channel when the fluid is delivered to the flow restrictor below a selected pressure; and a fitting body attached to the restrictor body proximate the downstream end of the restrictor body, wherein the fitting body comprises:

a fitting lumen, at least a portion of which is located within the outlet port lumen, the fitting lumen comprising a proximal end proximate the restrictor body and a distal end extending out of the outlet port;

a transverse passageway in fluid communication with the proximal end of the fitting lumen, wherein the transverse passageway comprises an opening proximate the downstream end of the restrictor body such that fluid exiting the groove at the downstream end of the restrictor body enters the transverse passageway through the opening and is passed through the fitting lumen to the distal end of the fitting body.

33. A branching catheter connector according to claim 32, wherein the fitting body and the restrictor body are a one-piece, completely integral unit.

34. A branching catheter connector according to claim 32, wherein the restrictor body has an interference fit within the outlet port lumen.

35. A branching catheter connector according to claim 32, further comprising a pump mechanism and reservoir in fluid communication with the inlet port.

36. A branching catheter connector for use in a branched medical catheter, the connector comprising:

an inlet port; and two or more outlet ports in fluid communication with the inlet port;

wherein each of the outlet ports comprises:

an outlet port lumen comprising an interior surface;

a flow restrictor located within the outlet port lumen, the flow restrictor comprising a restrictor body located within the outlet port lumen;

a channel located between an outer surface of the restrictor body and the interior surface of the outlet port lumen, wherein the channel extends from an upstream end of the restrictor body to a downstream end of the restrictor body, such that fluid passing through the outlet port lumen flows through the channel when the fluid is delivered to the flow restrictor below a selected pressure;

wherein the flow restrictor within at least one of the outlet ports comprises a pressure relief valve such that when the fluid is delivered to the flow restrictor above the selected pressure, fluid flows between the outer surface of the flow restrictor and the interior surface of the outlet port lumen outside of the channel.

37. A branching catheter connector according to claim 36, wherein the restrictor body has an interference fit within the outlet port lumen.

38. A branching catheter connector according to claim 36, further comprising a pump mechanism and reservoir in fluid communication with the inlet port.

39. A medical catheter system comprising:

a lumen;

a flow restrictor located within the lumen, the flow restrictor comprising one or more capillaries within the lumen, wherein each capillary of the one or more capillaries comprises a first opening at an upstream end of the flow restrictor and a second opening at a downstream end of the flow restrictor, wherein each capillary of the one or more capillaries comprises one or more coils within the lumen, and wherein fluid passing through the lumen from the upstream end to the downstream end of the flow restrictor flows through the one or more capillaries when the fluid is delivered to the upstream end of the flow restrictor below a selected pressure, wherein each capillary of the one or more capillaries comprises a substantially uniform diameter along a length of the capillary from the first opening to the second opening.

40. A medical catheter system comprising:

a lumen; and a flow restrictor located within the lumen, the flow restrictor comprising one or more capillaries within the lumen, wherein each capillary of the one or more capillaries comprises a first opening at an upstream end of the flow restrictor and a second opening at a downstream end of the flow restrictor, wherein each capillary of the one or more capillaries comprises one or more coils within the lumen, and wherein fluid passing through the lumen from the upstream end to the downstream end of the flow restrictor flows through the one or more capillaries when the fluid is delivered to the upstream end of the flow restrictor below a selected pressure, wherein the flow restrictor comprises a plug in which the one or more capillaries are contained, wherein the plug occludes the lumen such that fluid passing through the lumen from the upstream end of the flow restrictor to the downstream end of the flow restrictor passes through the one or more capillaries.

41. A method of providing pressure relief within a medical catheter system, the method comprising:

providing a medical catheter system that comprises:

a lumen comprising an interior lumen surface;

a flow restrictor located within the lumen, the flow restrictor comprising a restrictor body located within the lumen;

a channel located between an outer surface of the restrictor body and the interior lumen surface of the lumen, wherein the channel extends from an upstream end of the restrictor body to a downstream end of the restrictor body;

passing fluid through only the channel from the upstream end of the restrictor body to the downstream end of the restrictor body when fluid pressure within the lumen is below a selected pressure; and passing fluid between the outer surface of the restrictor body and the interior lumen surface of the lumen outside of the channel when fluid pressure is above the selected pressure.

42. A method according to claim 41, wherein passing fluid between the outer surface of the restrictor body and the interior lumen surface of the lumen above the selected pressure comprises enlarging the lumen around the restrictor body.

43. A method according to claim 41, wherein the fluid resumes flow through only the channel when the fluid pressure falls below the selected pressure after exceeding the selected pressure.

44. A method according to claim 41, wherein the channel is defined by a groove formed in the outer surface of the restrictor body, wherein the groove extends from the upstream end to the downstream end of the restrictor body.

45. A method according to claim 41, wherein the channel is defined by a groove formed in the interior lumen surface of the lumen, wherein the groove extends from the upstream end to the downstream end of the restrictor body.

46. A method according to claim 41, wherein the channel comprises a helical channel.

47. A method according to claim 41, wherein the flow restrictor comprises a first notch in the first end of the outer surface of the restrictor body, the first notch in fluid communication with the channel at the upstream end of the restrictor body.

48. A method according to claim 47, wherein the flow restrictor comprises a second notch in the second end of the outer surface of the restrictor body, the second notch in fluid communication with the channel at the downstream end of the restrictor body.

49. A method according to claim 41, wherein the restrictor body has an interference fit within the lumen.

50. A method according to claim 41, wherein the lumen is located within a branching catheter connector that comprises an inlet port and two or more outlet ports in fluid communication with the inlet port.

51. A method according to claim 41, wherein passing fluid between the outer surface of the restrictor body and the interior lumen surface of the lumen outside of the channel when fluid pressure is above the selected pressure results in increased fluid flow past the flow restrictor increases as compared to fluid flow past the flow restrictor when the fluid is delivered to the flow restrictor below the selected pressure.

* * * * *